(12) United States Patent
Goble et al.

(10) Patent No.: US 7,025,786 B2
(45) Date of Patent: *Apr. 11, 2006

(54) APPARATUS AND METHOD FOR RECONSTRUCTING A LIGAMENT

(75) Inventors: Eugene M. Goble, Alta, WY (US);
Daniel F. Justin, Logan, UT (US);
Alan Chervitz, Palm Harbor, FL (US);
T. Wade Fallin, Hyde Park, UT (US)

(73) Assignee: Ethicon, Inc., Somerville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/873,785

(22) Filed: Jun. 22, 2004

(65) Prior Publication Data

US 2004/0225358 A1   Nov. 11, 2004

Related U.S. Application Data

(63) Continuation of application No. 09/619,105, filed on Jul. 19, 2000, now Pat. No. 6,752,830.

(60) Provisional application No. 60/144,773, filed on Jul. 20, 1999.

(51) Int. Cl.
*A61F 2/08* (2006.01)
(52) U.S. Cl. ............... 623/13.14; 623/13.12; 606/72
(58) Field of Classification Search .............. 606/72, 606/73; 623/13.12, 13.14
See application file for complete search history.

(56) References Cited

U.S. PATENT DOCUMENTS

| | | | | |
|---|---|---|---|---|
| 4,901,711 A | * | 2/1990 | Goble et al. | 606/98 |
| 5,139,520 A | * | 8/1992 | Rosenberg | 606/87 |
| 5,266,075 A | * | 11/1993 | Clark et al. | 606/138 |
| 5,350,380 A | * | 9/1994 | Goble et al. | 606/80 |
| 5,354,300 A | * | 10/1994 | Goble et al. | 606/80 |
| 5,356,413 A | * | 10/1994 | Martins et al. | 606/75 |
| 5,393,302 A | * | 2/1995 | Clark et al. | 606/72 |
| 5,397,356 A | * | 3/1995 | Goble et al. | 606/73 |
| 5,431,651 A | * | 7/1995 | Goble | 606/73 |
| 5,562,671 A | * | 10/1996 | Goble et al. | 606/73 |
| 5,570,706 A | * | 11/1996 | Howell | 128/898 |
| 5,601,562 A | * | 2/1997 | Wolf et al. | 606/86 |
| 5,603,716 A | * | 2/1997 | Morgan et al. | 606/88 |
| 5,759,035 A | * | 6/1998 | Ricci | 433/174 |
| 5,849,013 A | * | 12/1998 | Whittaker et al. | 606/72 |
| 5,871,504 A | * | 2/1999 | Eaton et al. | 606/232 |
| 5,918,604 A | * | 7/1999 | Whelan | 128/898 |
| 6,113,604 A | * | 9/2000 | Whittaker et al. | 606/72 |
| 6,123,710 A | * | 9/2000 | Pinczewski et al. | 606/73 |
| 6,132,433 A | * | 10/2000 | Whelan | 606/72 |
| 6,152,928 A | * | 11/2000 | Wenstrom, Jr. | 606/72 |
| 6,267,767 B1 | * | 7/2001 | Strobel et al. | 606/104 |
| 6,280,472 B1 | * | 8/2001 | Boucher et al. | 623/13.11 |
| 6,306,138 B1 | * | 10/2001 | Clark et al. | 606/65 |

(Continued)

FOREIGN PATENT DOCUMENTS

EP   0376641 A1   7/1990

(Continued)

*Primary Examiner*—Ralph A. Lewis
(74) *Attorney, Agent, or Firm*—Pandiscio & Pandiscio

(57) ABSTRACT

A crosspin for supporting a graft ligament in a first bone tunnel formed in a bone. The crosspin is positioned in a second bone tunnel extending transverse to, and intersecting, the first bone tunnel. The crosspin is adapted to be drawn through the second bone tunnel by a flexible member attached to a distal portion of the cross pin. The crosspin includes a connector for releasably connecting the distal portion of the crosspin to an intermediate portion, such that the distal portion is separable from said intermediate portion.

5 Claims, 19 Drawing Sheets

U.S. PATENT DOCUMENTS

| | | | |
|---|---|---|---|
| 6,325,804 B1 * | 12/2001 | Wenstrom et al. | 606/72 |
| 6,379,384 B1 * | 4/2002 | McKernan et al. | 623/13.12 |
| 6,387,129 B1 * | 5/2002 | Rieser et al. | 623/13.14 |
| 6,436,100 B1 * | 8/2002 | Berger | 606/73 |
| 6,499,486 B1 | 12/2002 | Chervitz et al. | |
| 6,610,064 B1 | 8/2003 | Goble et al. | |
| 6,752,830 B1 * | 6/2004 | Goble et al. | 623/13.14 |
| 6,808,528 B1 | 10/2004 | Justin | |

FOREIGN PATENT DOCUMENTS

| | | | |
|---|---|---|---|
| EP | 0496140 A1 | | 7/1992 |
| EP | 0688185 B1 | | 12/1995 |
| EP | 0860146 B1 | | 8/1998 |
| GB | 2337463 A | | 11/1999 |
| WO | WO 99/15095 | * | 4/1999 |

* cited by examiner

APPARATUS AND METHOD FOR RECONSTRUCTING A LIGAMENT

REFERENCE TO PENDING PRIOR PATENT APPLICATION

This is a continuation of prior U.S. patent application Ser. No. 09/619,105, filed Jul. 19, 2000, now U.S. Pat. No. 6,752,830 by E. Marlowe Goble et al. for APPARATUS AND METHOD FOR RECONSTRUCTING A LIGAMENT, which in turn claims benefit of prior U.S. Provisional Patent Application Ser. No. 60/144,773, filed Jul. 20, 1999 by Eugene Marlowe Goble et al. for DEVICE AND METHOD TO HOLD GRAFT WITH A TRANSVERSE PIN.

FIELD OF THE INVENTION

This invention relates to medical devices and procedures in general, and more particularly to medical devices and procedures for reconstructing a ligament.

BACKGROUND OF THE INVENTION

A ligament is a piece of fibrous tissue which connects one bone to another.

Ligaments are frequently damaged (e.g., detached or torn or ruptured, etc.) as the result of injury and/or accident. A damaged ligament can impede proper motion of a joint and cause significant pain.

Various procedures have been developed to repair or replace a damaged ligament. The specific procedures used depend on the particular ligament which is to be restored and on the extent of the damage.

One ligament which is frequently damaged as the result of injury and/or accident is the anterior cruciate ligament (ACL). Looking now at FIG. 1, the ACL 5 extends between the top of the tibia 10 and the bottom of the femur 15. A damaged ACL can cause instability of the knee joint and cause substantial pain and arthritis.

Numerous procedures have been developed to restore the ACL through a graft ligament replacement. In general, and looking now at FIG. 2, these ACL replacement procedures involve drilling a bone tunnel 20 through tibia 10 and up into femur 15. Then a graft ligament 25, consisting of a harvested or artificial ligament or tendon(s), is passed through the tibial portion 30 of tunnel 20 (sometimes referred to as "the tibial tunnel"), across the interior of the joint, and up into the femoral portion 35 of tunnel 20 (sometimes referred to as "the femoral tunnel"). Then a distal portion of graft ligament 25 is secured in femoral tunnel 35, and a proximal portion of graft ligament 25 is secured in tibial tunnel 30.

OBJECTS OF THE INVENTION

One object of the present invention is to provide improved apparatus for positioning the graft ligament in the bone tunnel and/or for securing the graft ligament within the bone tunnel.

Another object of the present invention is to provide an improved method for reconstructing a ligament.

SUMMARY OF THE INVENTION

These and other objects of the present invention are addressed by novel apparatus and method for reconstructing a ligament.

In one preferred form of the invention, the invention comprises a crosspin for supporting a graft ligament in a first bone tunnel formed in a bone, by positioning the crosspin in a second bone tunnel extending transverse to, and intersecting, the first bone tunnel, the crosspin comprising: a shaft having a distal portion, in intermediate portion, and a proximal portion; the distal portion comprising attachment means for attaching a flexible member to the shaft; the intermediate portion comprising screw threads; and the proximal portion including driver engagement means for engagement by a driver adapted to turn the shaft; whereby the crosspin may be drawn through the second transverse bone tunnel by a flexible member attached to the distal portion by the attachment means, and the crosspin may have its screw threads turned into the bone by a driver engaged with the engagement means.

In another form of the invention, the invention comprises a crosspin for supporting a graft ligament in a first bone tunnel formed in a bone, by positioning the crosspin in a second bone tunnel extending transverse to, and intersecting, the first bone tunnel, the crosspin comprising: a shaft having a distal portion, in intermediate portion, and a proximal portion; the distal portion having a flexible member attached thereto; the intermediate portion comprising screw threads; and the proximal portion including driver engagement means for engagement by a driver adapted to turn the shaft; whereby the crosspin may be drawn through the second transverse bone tunnel by the flexible member, and the crosspin may have its screw threads turned into the bone by a driver engaged with the engagement means.

In another form of the invention, the invention comprises a crosspin for supporting a graft ligament in a first bone tunnel formed in a bone, by positioning the crosspin in a second bone tunnel extending transverse to, and intersecting, the first bone tunnel, the crosspin comprising: a cannulated shaft having a distal portion, in intermediate portion, and a proximal portion; the intermediate portion comprising screw threads; and the proximal portion including driver engagement means for engagement by a driver adapted to turn the shaft; whereby the crosspin may be positioned in the second transverse bone tunnel by loading the crosspin on, and moving the crosspin along, the flexible member, and the crosspin may have its screw threads turned into the bone by a driver engaged with the engagement means.

In another form of the invention, the invention comprises a method for securing a graft ligament in a bone tunnel, wherein the graft ligament comprises a bone block and a ligament attached to the bone block, the method comprising the steps of: (1) forming a first bone tunnel in a bone, and forming a second bone tunnel in the same bone, the second bone tunnel being transverse to, and intersecting, the first bone tunnel; and (2) positioning the graft ligament in the first bone tunnel, and positioning a crosspin in the second transverse bone tunnel, so that the bone block is positioned in the first bone tunnel on one side of the crosspin and the ligament is positioned in the first bone tunnel so that the ligament extends past the crosspin to the other side of the crosspin, whereby when tension is applied to the end of the ligament opposite from the bone block, the bone block will be stopped from movement past the crosspin by engagement of the bone block with the crosspin.

In another form of the invention, the invention comprises a method for securing a graft ligament in a bone tunnel, wherein the graft ligament comprises a bone block and a ligament attached to the bone block, the method comprising the steps of: (1) forming a first bone tunnel in a bone, and forming a second bone tunnel in the same bone, the second bone tunnel being transverse to, and intersecting, the first bone tunnel; and (2) positioning the graft ligament in the first bone tunnel, and positioning a crosspin in the second transverse bone tunnel, so that the bone block is positioned in the first bone tunnel on one side of the crosspin, and the ligament is positioned in the first bone tunnel so that the ligament extends past the crosspin to the other side of the crosspin, loops over the crosspin, and extends past the crosspin back to the first side of the crosspin, whereby when tension is applied to the end of the ligament opposite from the bone block, the bone block will be stopped from movement past the crosspin by engagement of the bone block with the crosspin.

In another form of the invention, the invention comprises apparatus for securing a graft ligament in a bone tunnel, wherein the graft ligament comprises a bone block and a ligament attached to the bone block, the apparatus comprising: a plate having a body with an opening formed therein, and a plurality of pointed legs extending therefrom, the body being sized to receive the bone block between the pointed legs; and a crosspin comprising a shaft and screw threads formed thereon, the shaft being sized to pass through the opening such that the crosspin may secure the bone block to the wall of the bone tunnel.

In another form of the invention, the invention comprises a method for securing a graft ligament in a bone tunnel, wherein the graft ligament comprises a bone block and a ligament attached to the bone block, the method comprising the steps of: (1) forming a first bone tunnel in a bone, and forming a second bone tunnel in the same bone, the second bone tunnel being transverse to, and intersecting, the first bone tunnel, and providing a plate having a body with an opening formed therein, and a plurality of pointed legs extending therefrom, the body being sized to receive the bone block between the pointed legs, and providing a crosspin comprising a shaft and screw threads formed thereon; (2) positioning the graft ligament and the plate in the first bone tunnel, and positioning the crosspin in the second transverse bone tunnel, so that the crosspin extends through the opening in the plate and urges the plate against the bone block, whereby the graft ligament will be secured in the first bone tunnel.

BRIEF DESCRIPTION OF THE DRAWINGS

The above and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE INVENTION

Non-Cannulated Crosspin

In one form of the invention, there is provided a novel non-cannulated crosspin for supporting a graft ligament in a bone tunnel.

Figure 1:
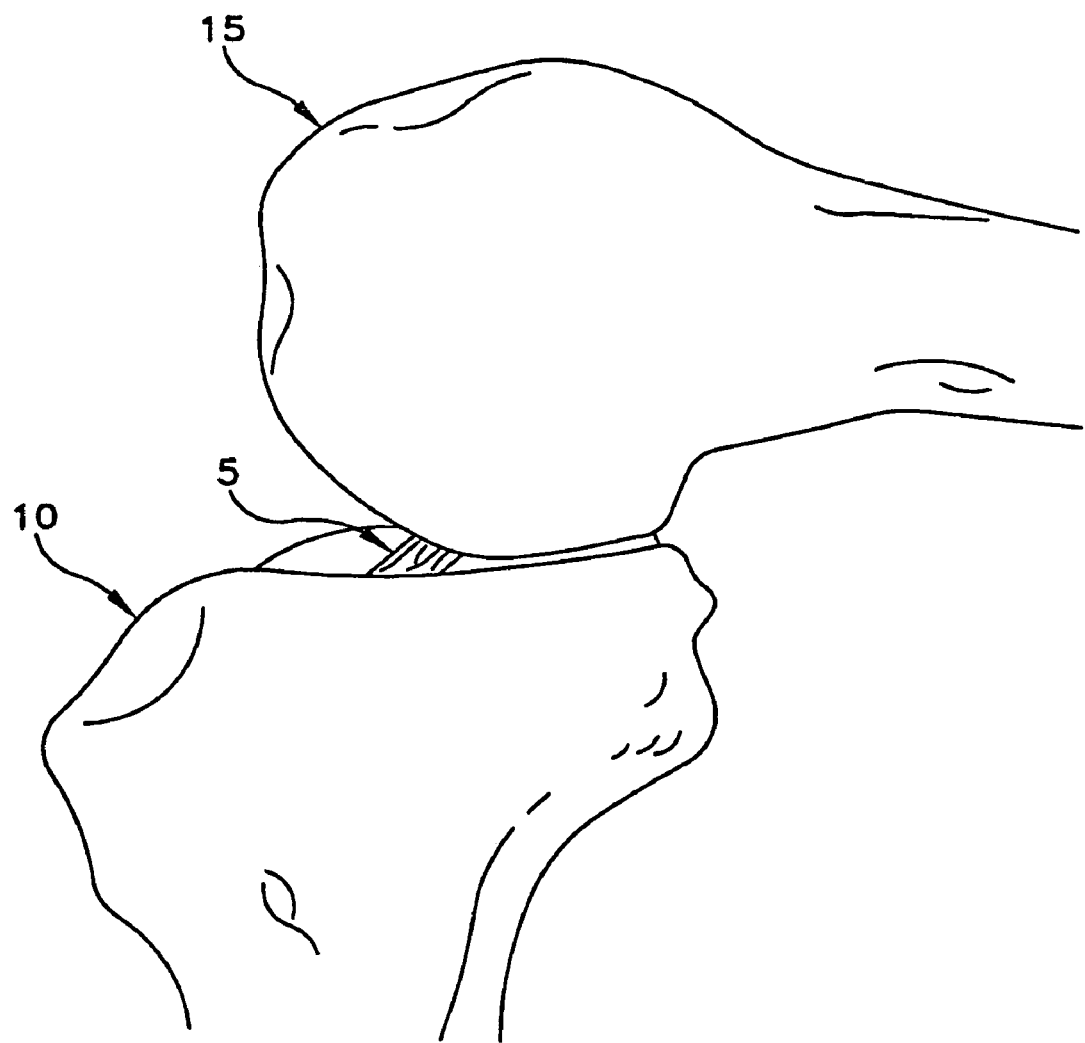
FIG. 1 is a schematic side view of a knee joint, showing an ACL extending between the top of the tibia and the bottom of the femur.
Figure 2:
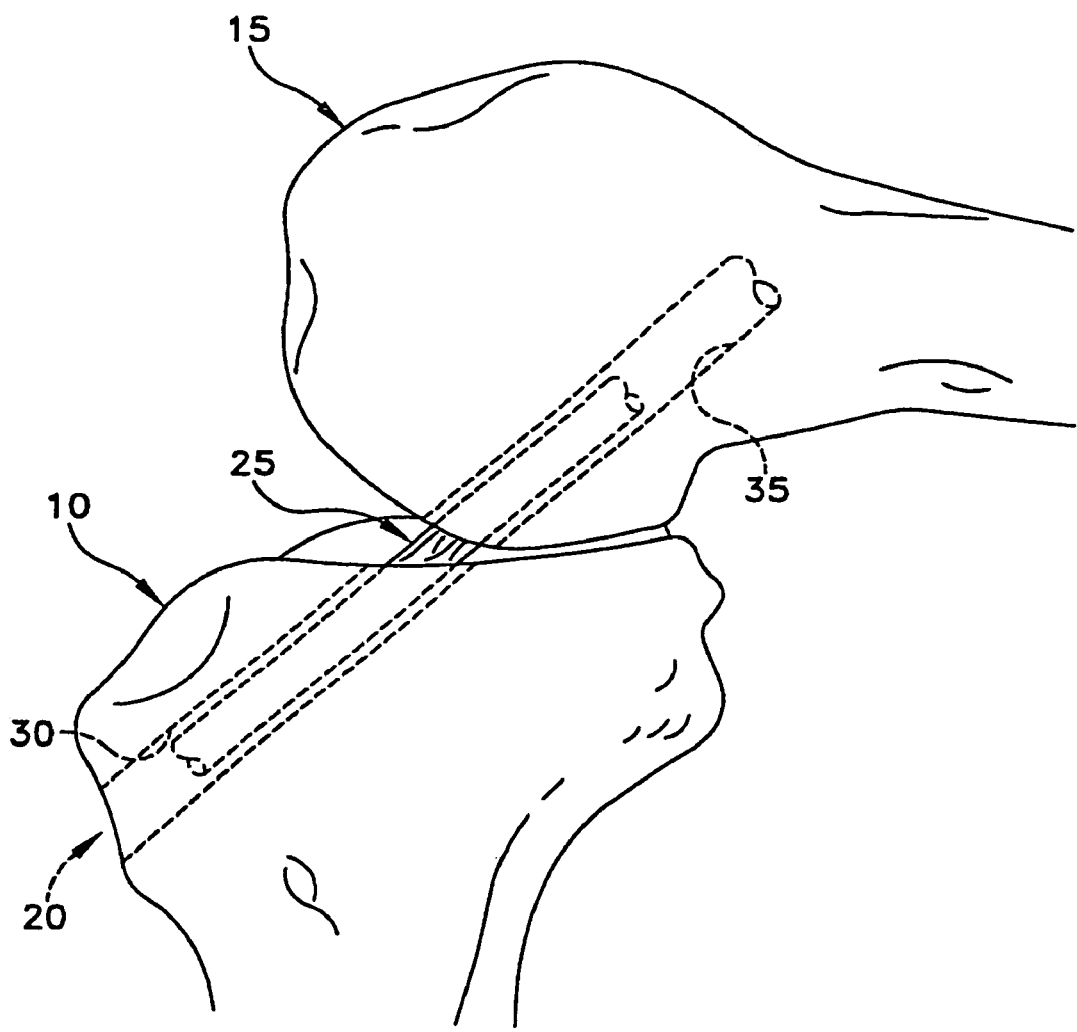
FIG. 2 is a schematic side view of the same knee joint, except showing portions of an ACL reconstruction.
Figure 3:
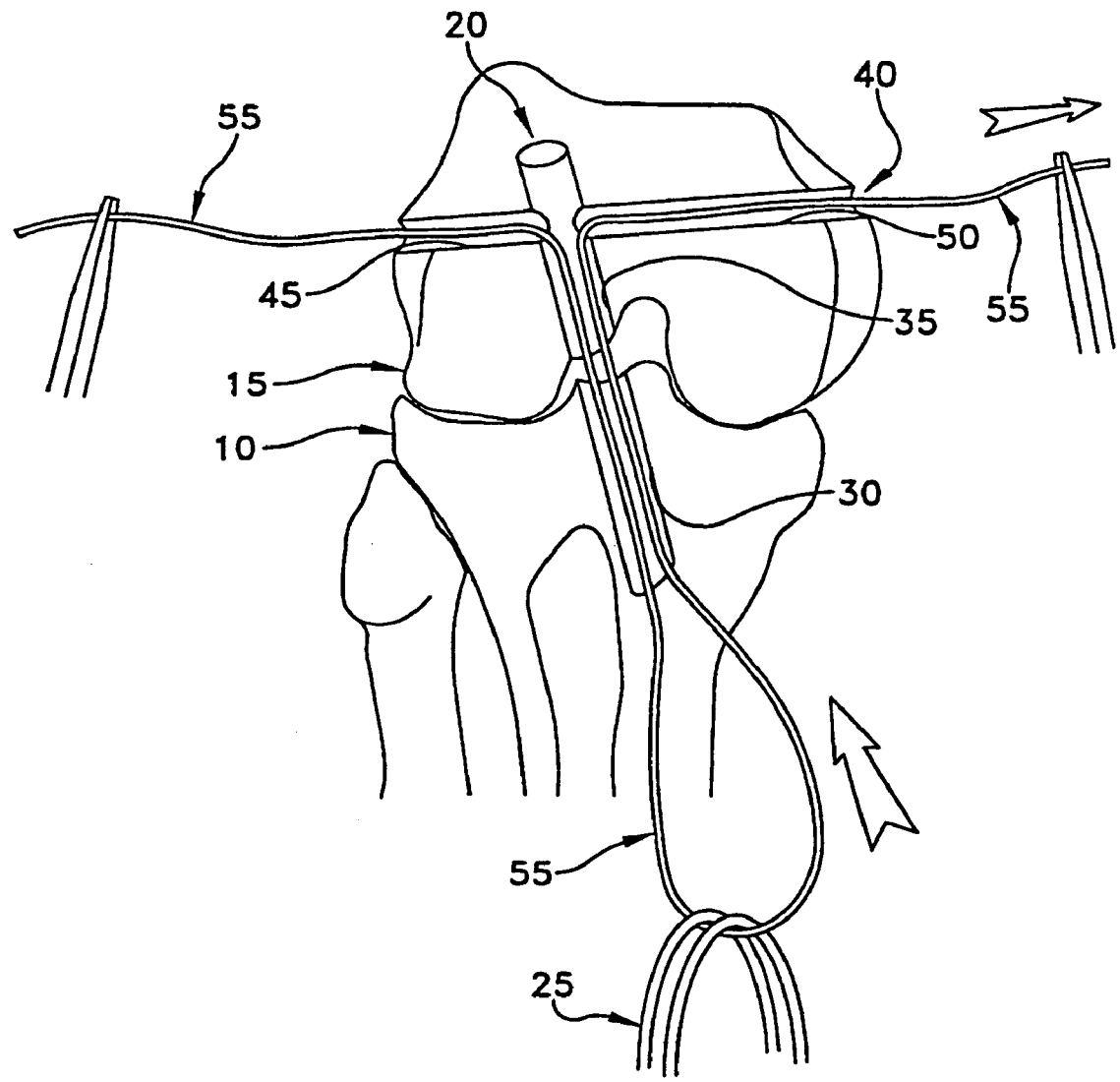
FIGS. 3–7 are schematic front views of a knee joint, illustrating a crosspinning procedure utilizing a first type of crosspin.

More particularly, and looking now at FIG. 3, during one type of ACL reconstruction, the bone tunnel 20 is formed by drilling through tibia 10 and up into femur 15, whereby to form tibial tunnel 30 and femoral tunnel 35. Then a transverse bone tunnel 40 is formed in femur 15 so that transverse bone tunnel 40 intersects femoral tunnel 35. Bone tunnel 20 bifurcates transverse bone tunnel 40 into two tunnel portions, a first transverse bone tunnel portion 45 and a second transverse bone tunnel portion 50.

After transverse bone tunnel 40 has been formed, a flexible member 55 is used to draw graft ligament 25 up into place.

There are a number of ways that this may be accomplished and, for the purposes of the present invention, all are satisfactory. However, for purposes of example but not limitation, a particular method for drawing graft ligament 25 into place using flexible member 55 will now be reviewed.

First, flexible member 55 is threaded through transverse bone tunnel 40. Then a crochet-hook device (not shown) is passed up tibial tunnel 30, across the interior of the knee joint, and up femoral tunnel 35. The crochet-hook device is used to hook flexible member 55 at the intersection of bone tunnel 20 and transverse bone tunnel 40. Then the crochet-hook device is used to pull flexible member 55 down femoral tunnel 35, across the interior of the knee joint, down tibial tunnel 30, and out the front side of tibia 10. Next, graft ligament 25 is looped over flexible member 55 (FIG. 3). If desired, graft ligament 25 can be secured around flexible member 55 by a suture, a clip or a tie device (not shown) so as to prevent graft ligament 25 from slipping off flexible member 55. Flexible member 55 is then used to pull the looped graft ligament 25 up tibial tunnel 30, across the interior of the knee joint, and then up into femoral tunnel 35 (FIG. 4).

Figure 4:
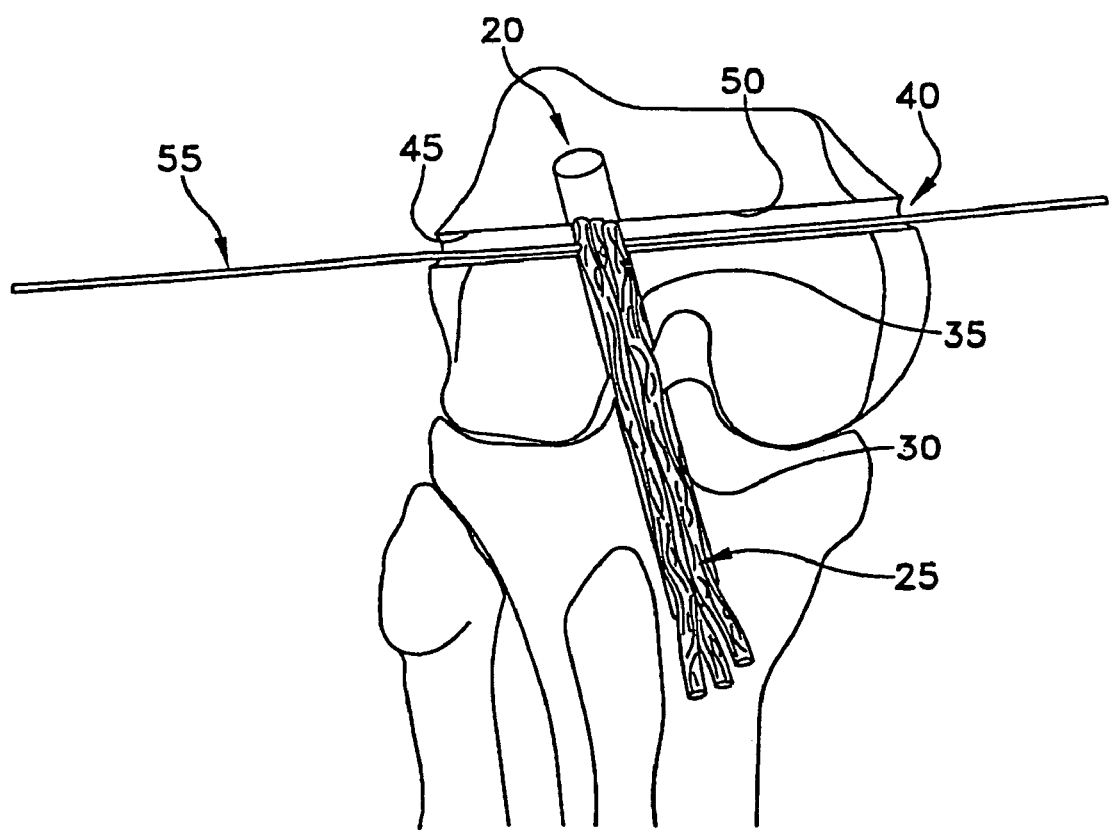

Once graft ligament 25 and flexible member 55 have assumed the position shown in FIG. 4, the graft ligament may be retained in that position through the use of a novel non-cannulated crosspin.

Figure 5:
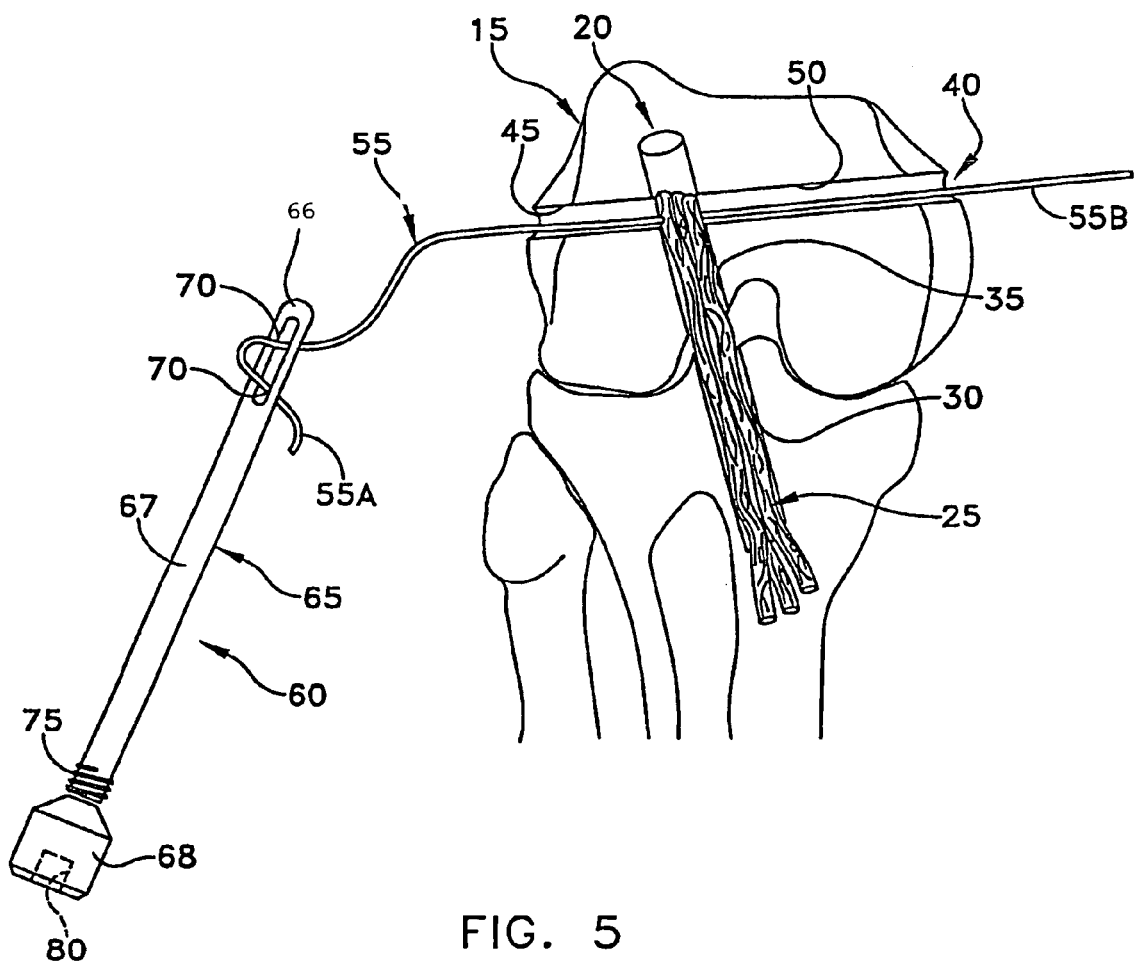
Figure 6:
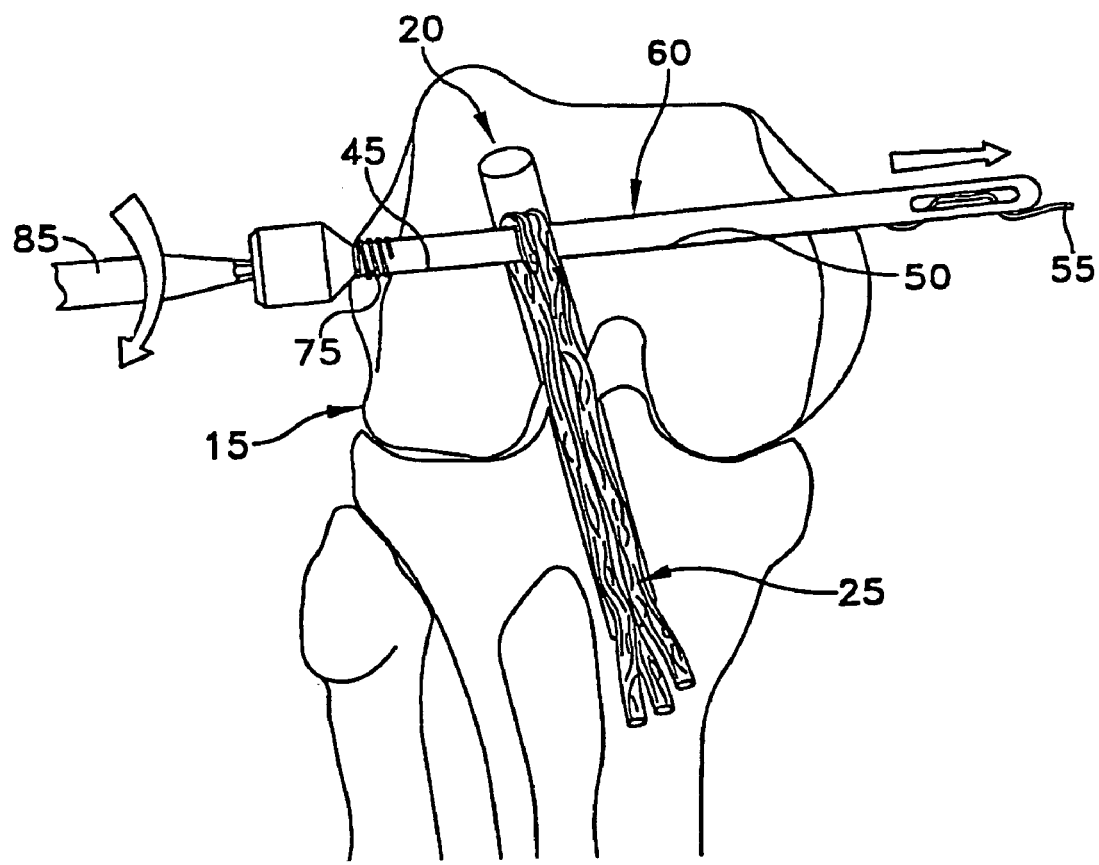
Figure 7:
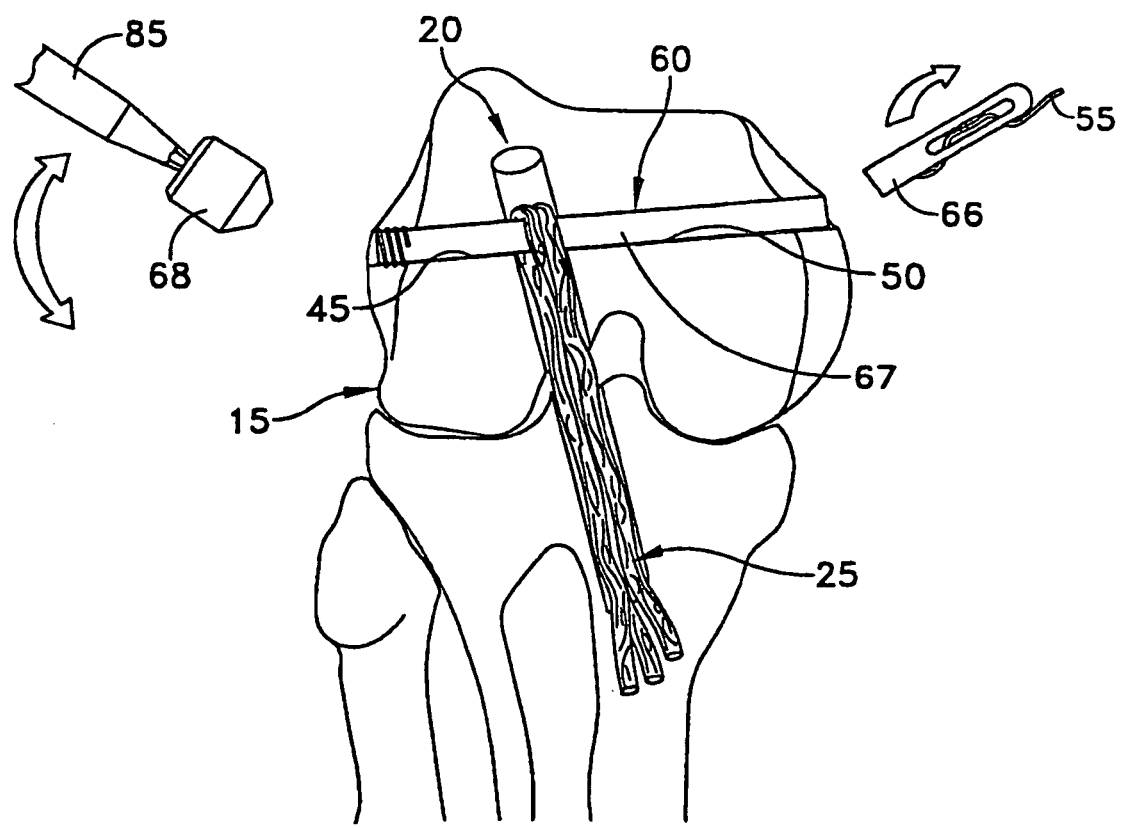

More particularly, and looking now at FIGS. 5–7, graft ligament 25 may be supported in femoral tunnel 35 with a novel crosspin 60. Crosspin 60 generally comprises a solid shaft 65 having a distal portion 66, an intermediate portion 67 and a proximal portion 68. One or more openings 70 are formed in the shaft's distal portion 66, and screw threads 75 are formed in the shaft's intermediate portion 67, adjacent to proximal portion 68. Crosspin 60 also comprises a recess 80 in its proximal portion 68 for receiving the front end of a driver 85 (FIG. 6).

Crosspin 60 is deployed by (1) attaching one end, 55A, of flexible member 55 to crosspin 60 using openings 70 (FIG. 5); (2) drawing crosspin 60 across first transverse bone tunnel portion 45, under the looped graft ligament 25, across second transverse bone tunnel portion 50, and out the far side of transverse bone tunnel 40, until the crosspin's screw threads 75 engage femur 15; (3) turning crosspin 60 with driver 85 so that threads 75 are set into femur 15 (FIG. 6); and (4) removing the distal and proximal portions of crosspin 60 that extend beyond the outside surfaces of femur 15 (FIG. 7).

Non-Cannulated Crosspin with Pre-Attached Flexible Member

Figure 8:
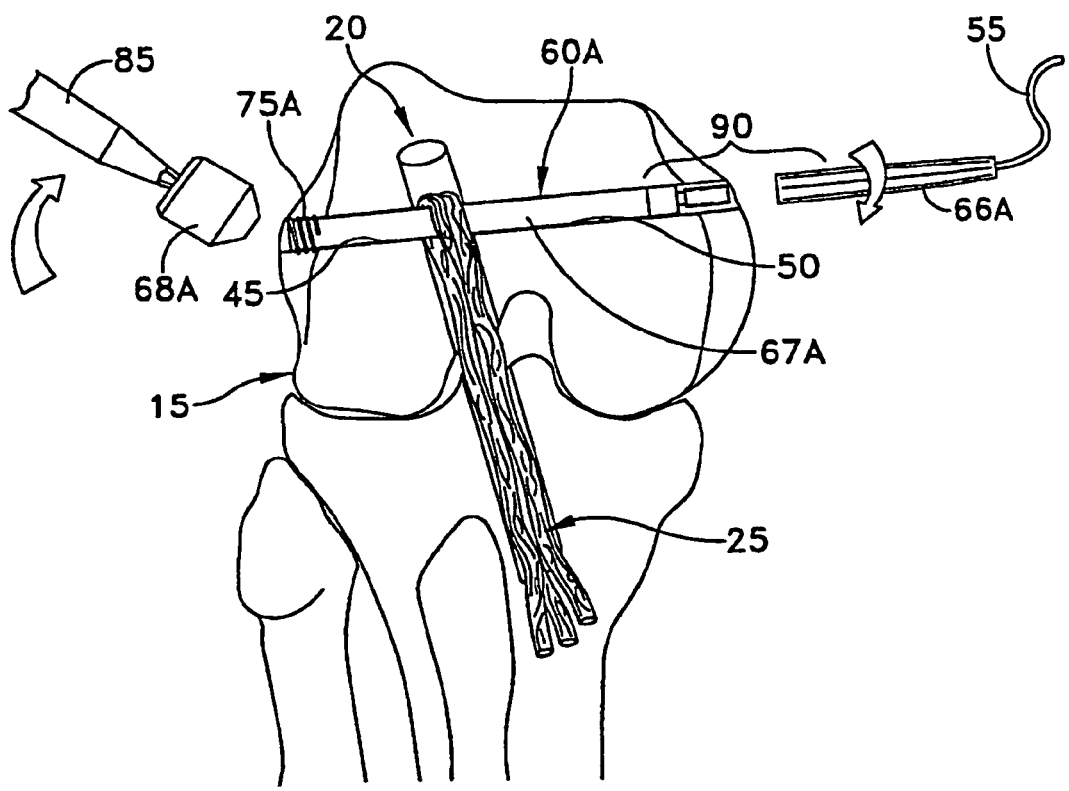
FIG. 8 is a schematic front view of a knee joint, illustrating a crosspinning procedure utilizing a second type of crosspin.

Looking next at FIG. 8, there is shown a novel non-cannulated crosspin 60A which is similar to the crosspin 60 described above, except that the distal portion 66A of crosspin 60A has flexible member 55 permanently attached thereto. Thus, with crosspin 60A, flexible member 55 does not need to be connected to the crosspin at the time of use, as is the case with the crosspin 60 discussed above. With this one exception, crosspin 60A is intended to be used in substantially the same way as the crosspin 60 discussed above.

As an additional alternative construction, distal portion 66A of crosspin 60A may be joined to intermediate portion 67A of the crosspin through a male/female screw mount, such as is shown generally at 90. Such a feature facilitates removal of distal portion 66A from intermediate portion 67A after the crosspin has been set in femur 15. Of course, if desired, such a screw mount may also be incorporated into the construction of the crosspin 60 discussed above.

Cannulated Crosspin

Figure 9:
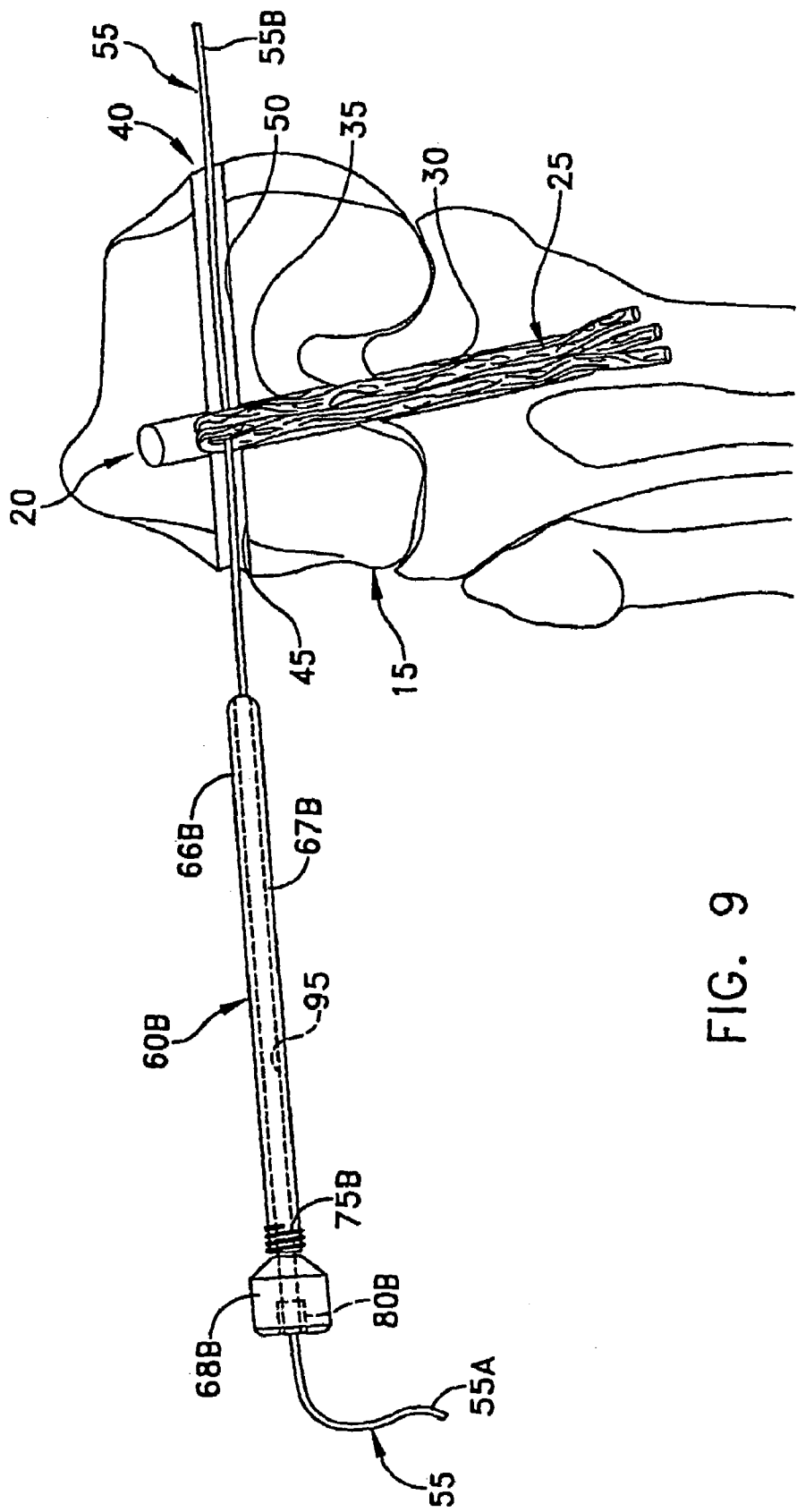
FIG. 9 is a schematic front view of a knee joint, illustrating a crosspinning procedure utilizing a third type of crosspin.

Looking next at FIG. 9, there is shown a novel cannulated crosspin 60B. Crosspin 60B is identical to the crosspin 60 discussed above, except that (1) crosspin 60B lacks the openings 70 formed in the distal portion 66 of the crosspin 60 discussed above, and (2) crosspin 60B is cannulated along its length with a longitudinal bore 95.

In use, flexible member 55 and graft ligament 25 are first positioned in the manner shown in FIG. 4, and then crosspin 60B is slipped over the free end 55A of flexible member 55, with flexible member 55 being received in the crosspin's longitudinal bore 95. Crosspin 60B is then advanced along flexible member 55 so that the crosspin passes through first transverse bone tunnel portion 45, under the looped graft ligament 25, and through second transverse bone tunnel portion 50, until the crosspin's threads 75B engage the outer surface of femur 15. A cannulated driver (not shown, but similar to the driver 85 shown in FIGS. 6–8, except that it is cannulated) is then loaded over the free end 55A of flexible member 55, advanced along flexible member 55, and then used to advance crosspin 60B so that the crosspin's screw threads 75B are set in femur 15. The cannulated driver is then withdrawn, flexible member 55 is removed, and the crosspin's protruding distal portion 66B and proximal portion 60B trimmed off so as to complete the crosspinning procedure.

Crosspinning a Graft Ligament Comprising a Bone Block

In another novel aspect of the present invention, and looking now at FIGS. 10–18, there is disclosed a novel method for crosspinning a graft ligament comprising a bone block.

More particularly, in the preceding sections, the present invention has been discussed in the context of a graft ligament 25 comprising a loop of soft tissue, e.g., a hamstring tendon. However, it is also possible to crosspin a graft ligament comprising a bone block.

Figure 11:
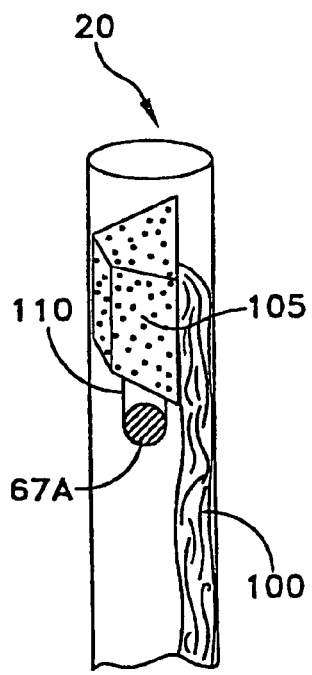
FIGS. 10–12 are schematic views illustrating a crosspinning procedure utilizing a graft ligament comprising a bone block.
Figure 10:
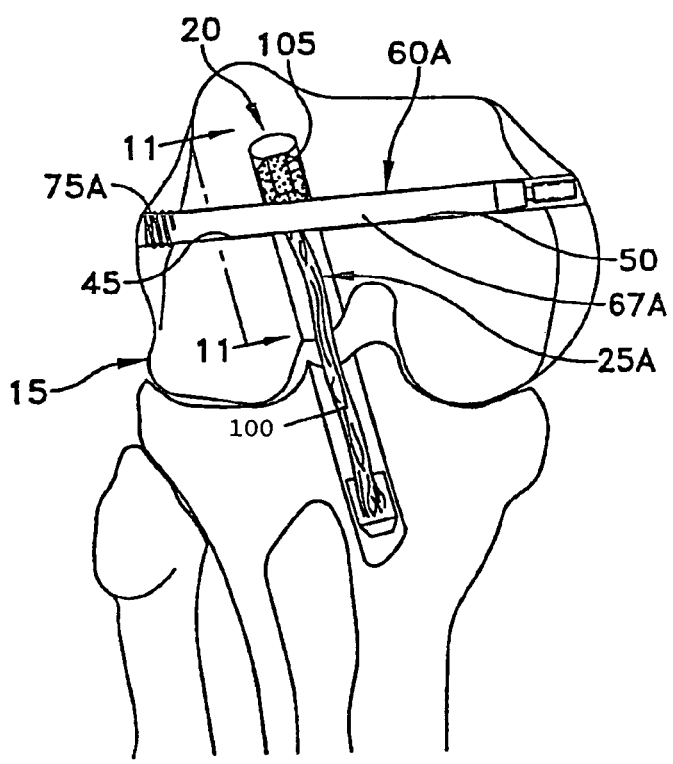

More particularly, and looking now at FIGS. 10 and 11, there is shown a graft ligament 25A comprising a ligament 100 and a bone block 105. By way of example but not limitation, graft ligament 25A might be a patellar graft comprising a portion of the patella tendon and a portion of the patella. Such graft ligaments are sometimes preferred since ligament 100 is naturally, and hence securely, attached to bone block 105, and since it is relatively easy to achieve good osseointegration between bone block 105 and femur 15.

In accordance with a teaching of the present invention, graft ligament 25A is positioned in bone tunnel 20 so that bone block 105 resides distal to crosspin 60A, i.e., so that bone block 105 resides outboard of crosspin 60A relative to the interior of the joint. As a result, when graft ligament 25A is thereafter placed under tension, crosspin 60A will prevent the bone block 105 from passing by the crosspin, whereby graft ligament 25A will be maintained in position.

Figure 12:
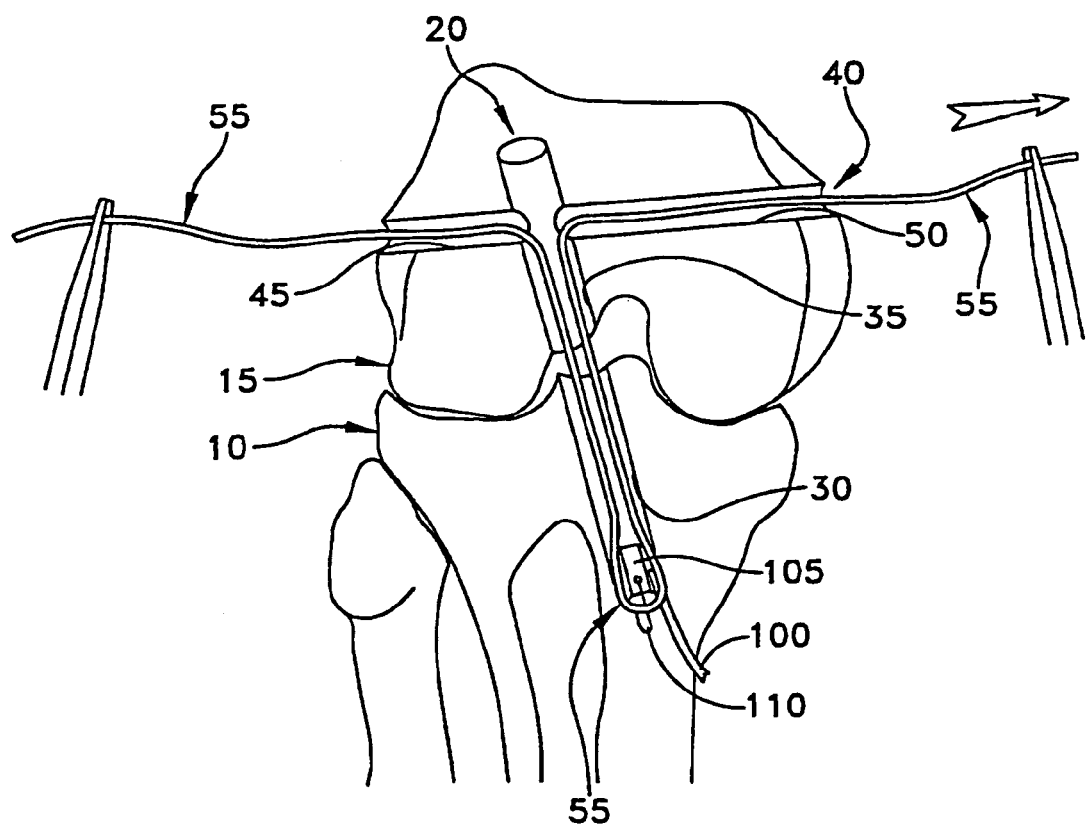

FIG. 12 illustrates how graft ligament 25A may be loaded onto flexible member 55 so that it achieves the position shown in FIGS. 10 and 11. If desired, a suture 110 (FIGS. 11 and 12) may be used to help keep graft ligament 25A properly positioned relative to flexible member 55 and, subsequently, crosspin 60A.

Figures 13, 14:
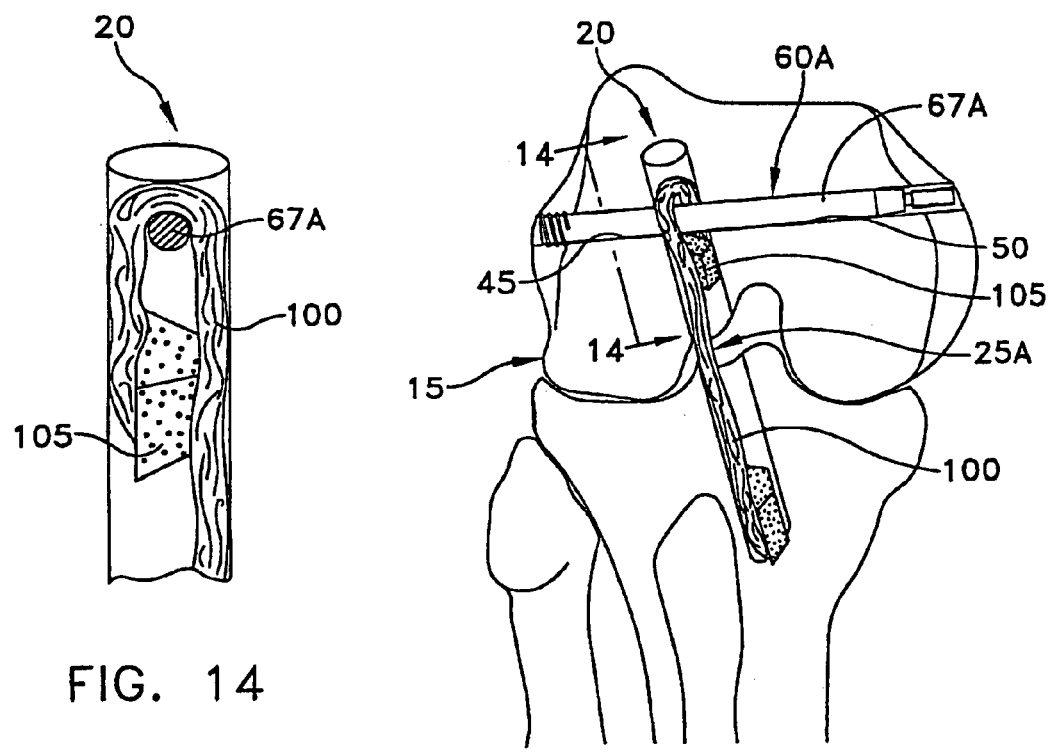
FIGS. 13–15 are schematic views illustrating another crosspinning procedure utilizing a graft ligament comprising a bone block.

Similarly, and looking now at FIGS. 13 and 14, the graft ligament 25A may also be secured in position by positioning bone block 105 proximal to crosspin 60A, with ligament lob looping over crosspin 60A before passing proximally out of femoral tunnel 35. As a result, when graft ligament 25A is thereafter placed under tension, crosspin 60A will prevent the bone block 105 from passing by the crosspin, whereby graft ligament 25A will be maintained in position.

Figure 15:
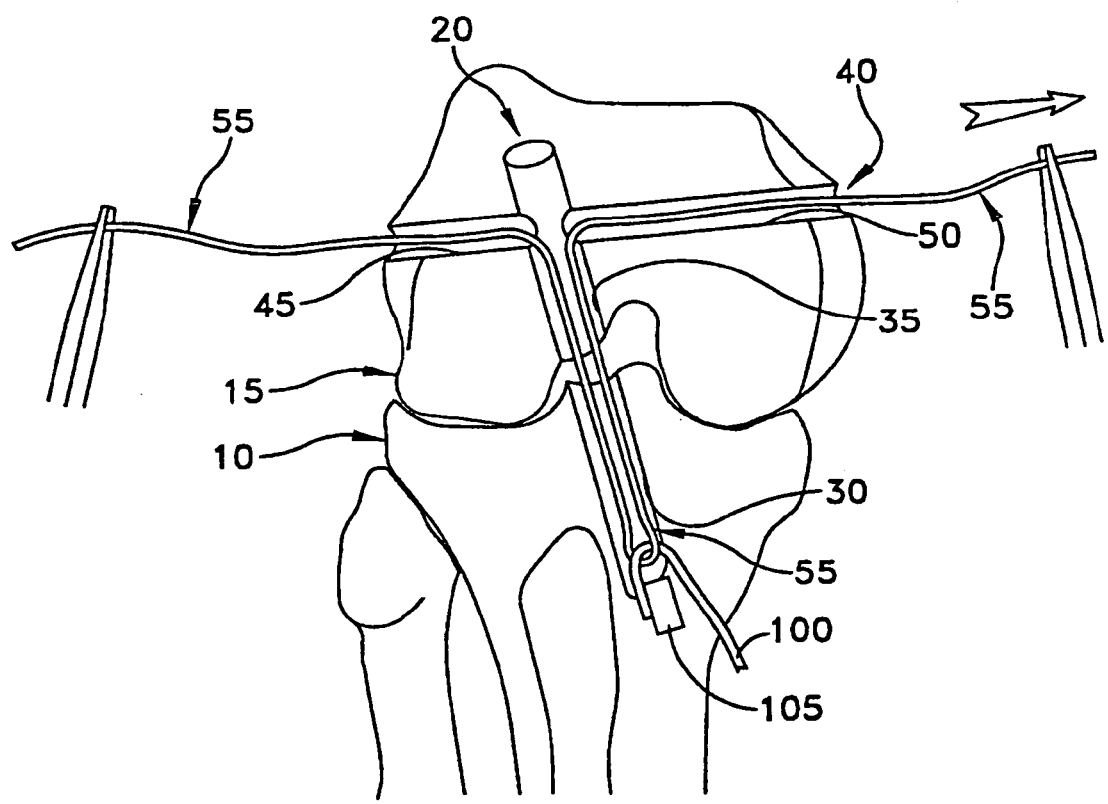

FIG. 15 illustrates how graft ligament 25A may be loaded onto flexible member 55 so that it subsequently achieves the position shown in FIGS. 13 and 14 with respect to crosspin 60A.

Figures 16, 17:
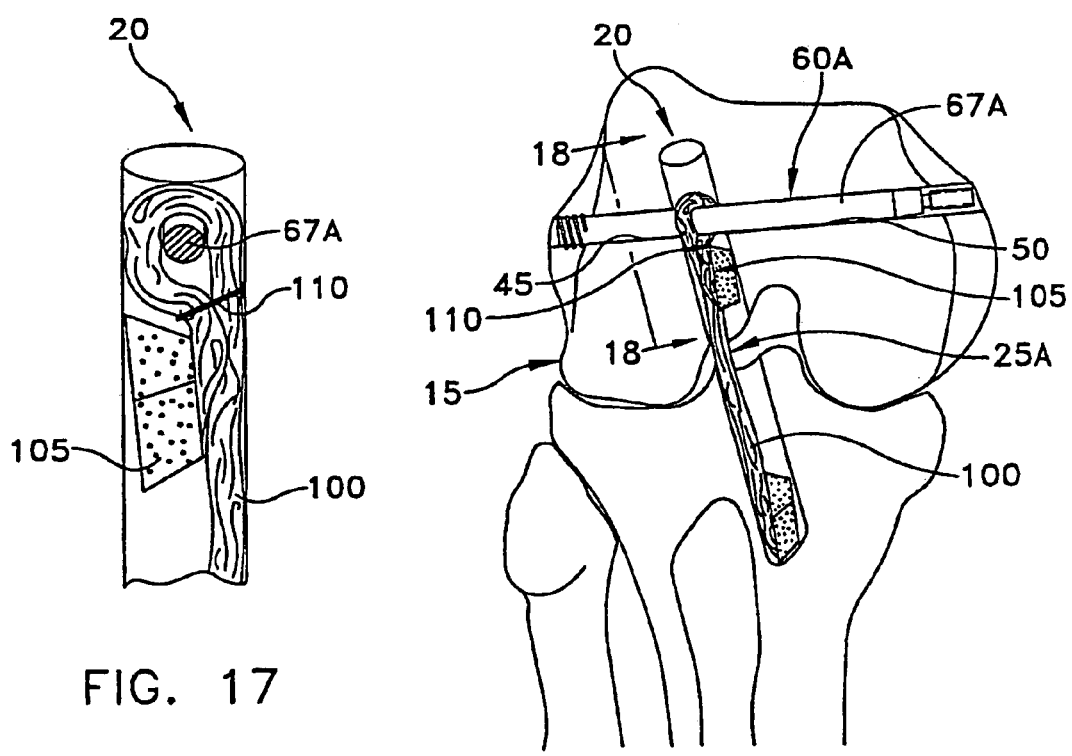
FIGS. 16–18 are schematic views illustrating still another crosspinning procedure utilizing a graft ligament comprising a bone block.
Figure 18:
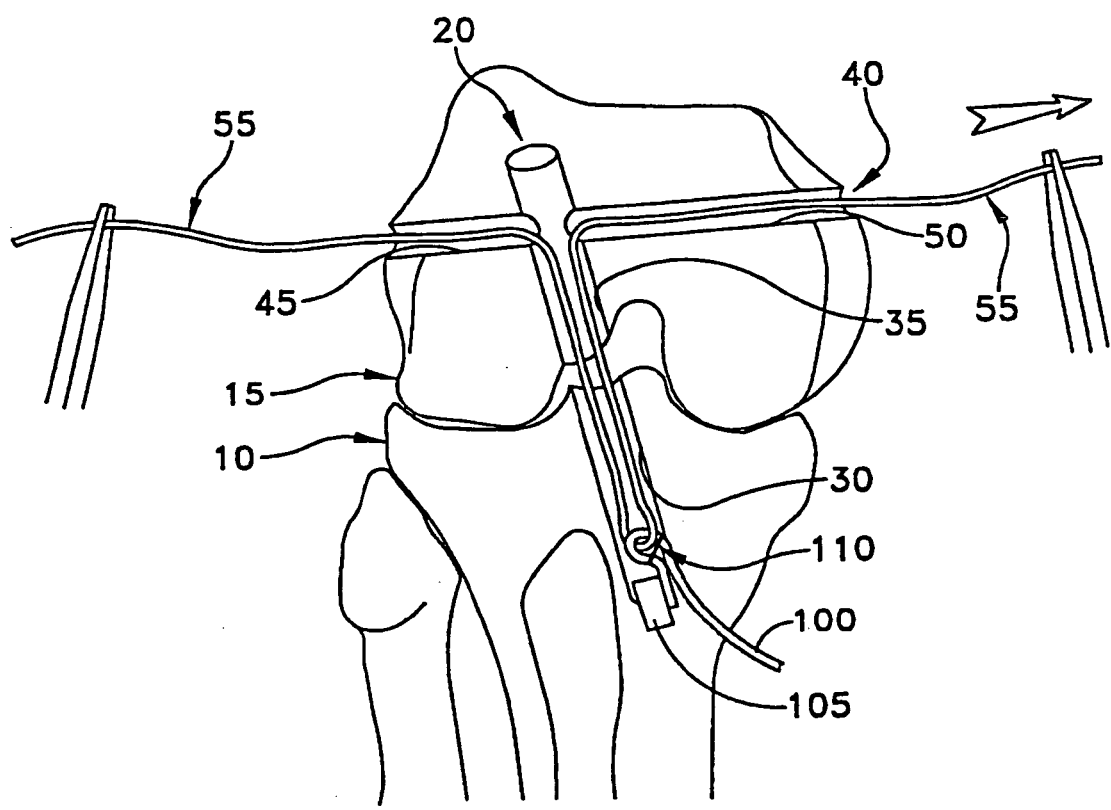

Furthermore, and looking now at FIGS. 16 and 17, if desired, a suture 110 may be used to hold the graft ligament in a looped form. Again, FIG. 18 illustrates how graft ligament 25A may be loaded onto flexible member 55 so that it subsequently achieves the position shown in FIGS. 16 and 17 with respect to crosspin 60A.

With respect to the bone-block-based crosspinning techniques described above and illustrated in FIGS. 10–18, it should also be appreciated that while the techniques have been discussed in the context of the aforementioned crosspin 60A, they may also be practiced equally well with the crosspins 60 and 60B discussed above, as well as with other crosspins well known in the art.

Figure 19:
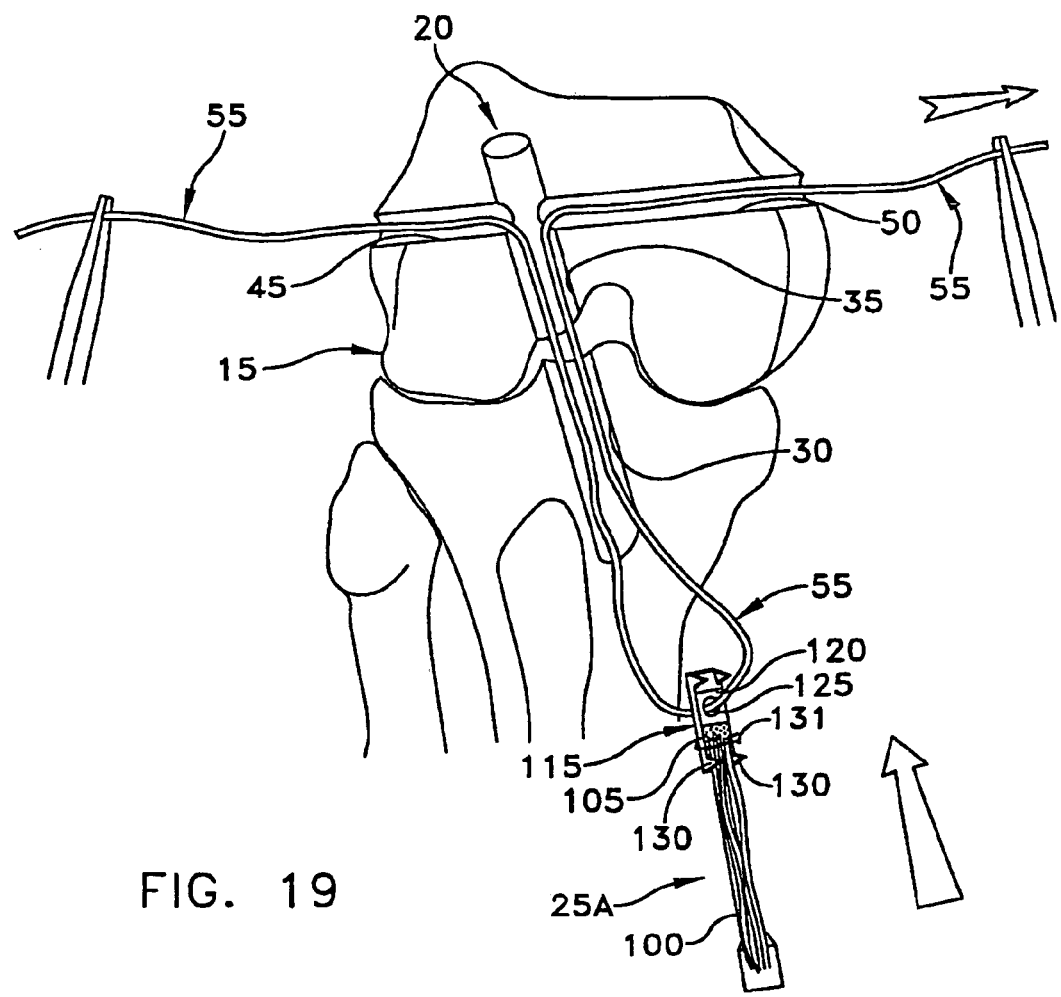
FIGS. 19–21 are schematic views illustrating a crosspinning procedure utilizing a plate and a graft ligament comprising a bone block.
Figure 20:
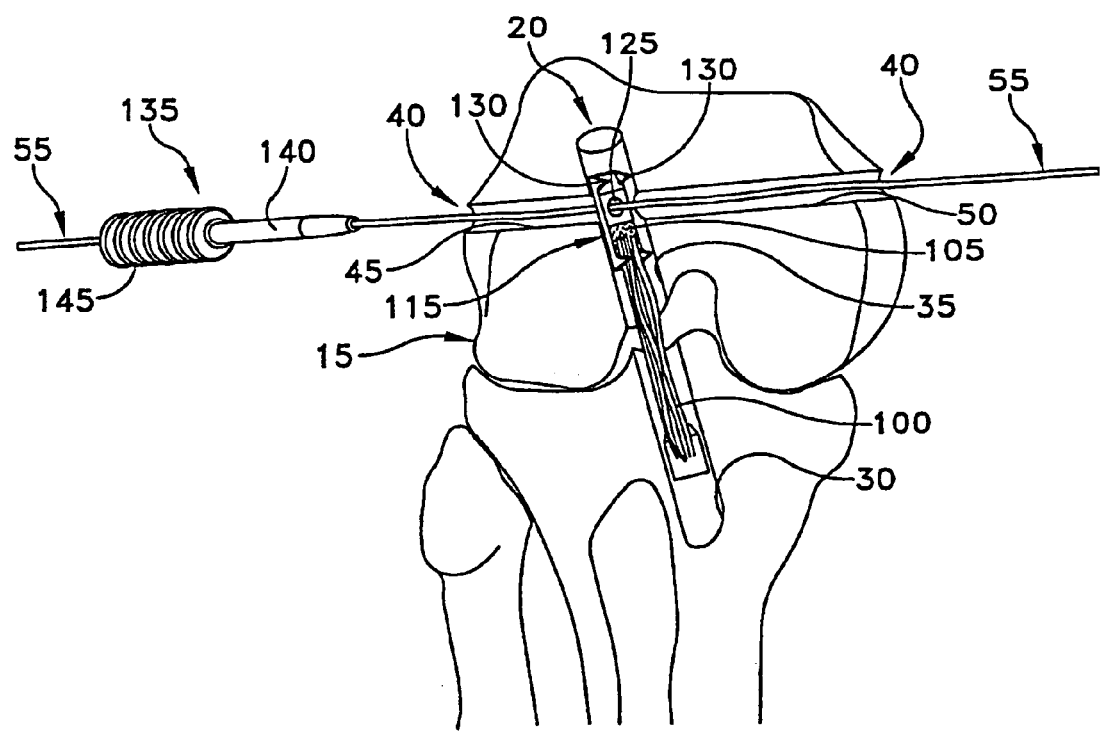
Figure 21:
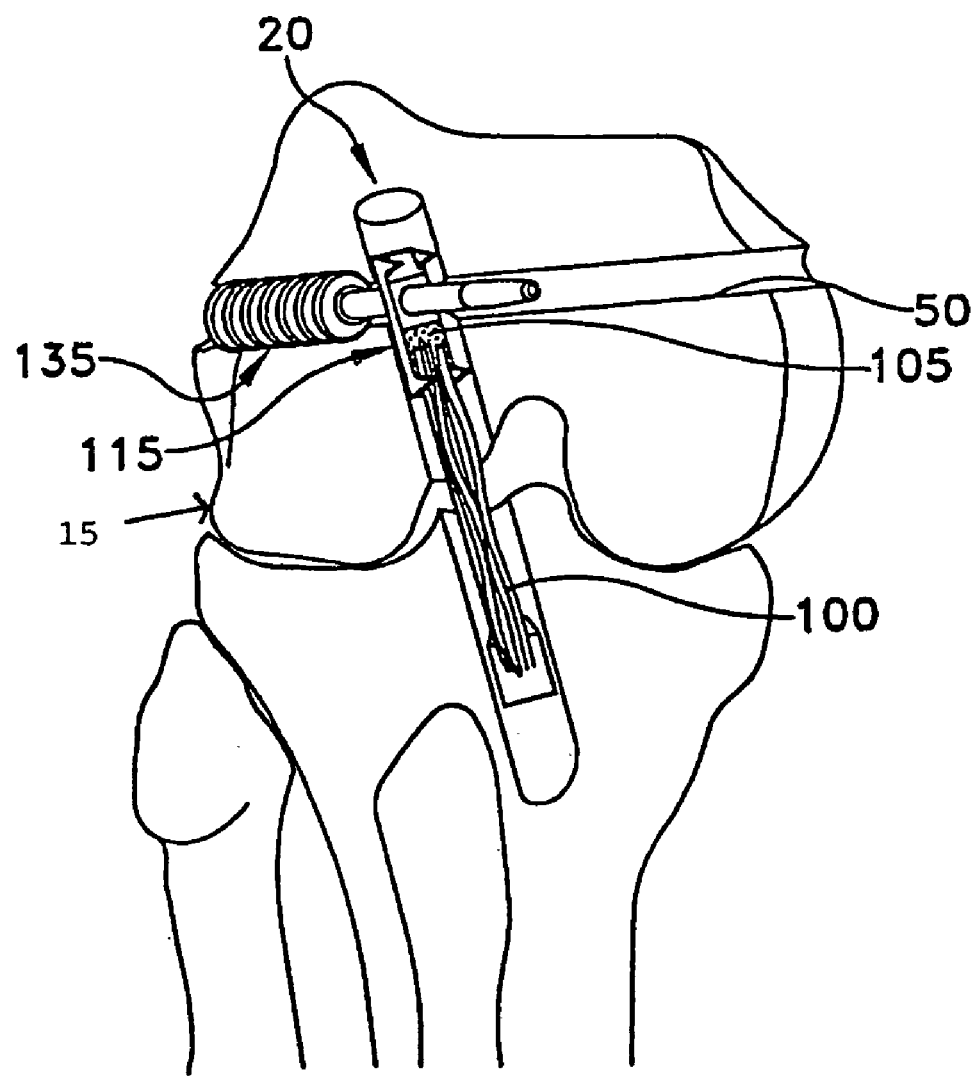

Crosspinning Procedure Utilizing a Plate and a Graft Ligament Comprising a Bone Block In yet another preferred embodiment of the present invention, and looking now at FIGS. 19–21, there is shown a plate 115 which may be used to secure bone block 105 of graft ligament 25A to femur 15. Plate 115 comprises a body portion 120, an opening 125 formed in body portion 120, and a plurality of pointed legs 130.

Plate 115 is arranged to have flexible member 55 passed through opening 125, and bone block 105 seated against body portion 120 (FIG. 19), with or without a securing suture 131, whereby flexible member 55 may be used to draw plate 115, and hence graft ligament 25A, up into position in femur 15 (FIG. 20) Thereafter, a cannulated crosspin 135, comprising a shaft 140 and enlarged screw threads 145, is passed over flexible member 55 and into first transverse bone tunnel portion 45. Crosspin 135 is then advanced within transverse bone tunnel 40 so that the crosspin's shaft 140 passes through opening 125 in plate 115 and into second transverse bone tunnel portion 50, and so that the crosspin's enlarged screw threads 145 engage the outside surface of femur 15. A cannulated driver (not shown) is then used to advance crosspin 135 further into transverse bone tunnel 40. By sizing the plate's opening 125 so that it will make a snug fit with the crosspin's shaft 140, the crosspin will drive plate 115 laterally, whereby to drive the plate's pointed legs 130 into the side wall of femoral tunnel 35, and whereby to hold bone block 105 securely against the side wall of the bone tunnel (FIG. 21). Flexible member 55 may thereafter be removed so as to complete the crosspinning procedure.

Figure 22:
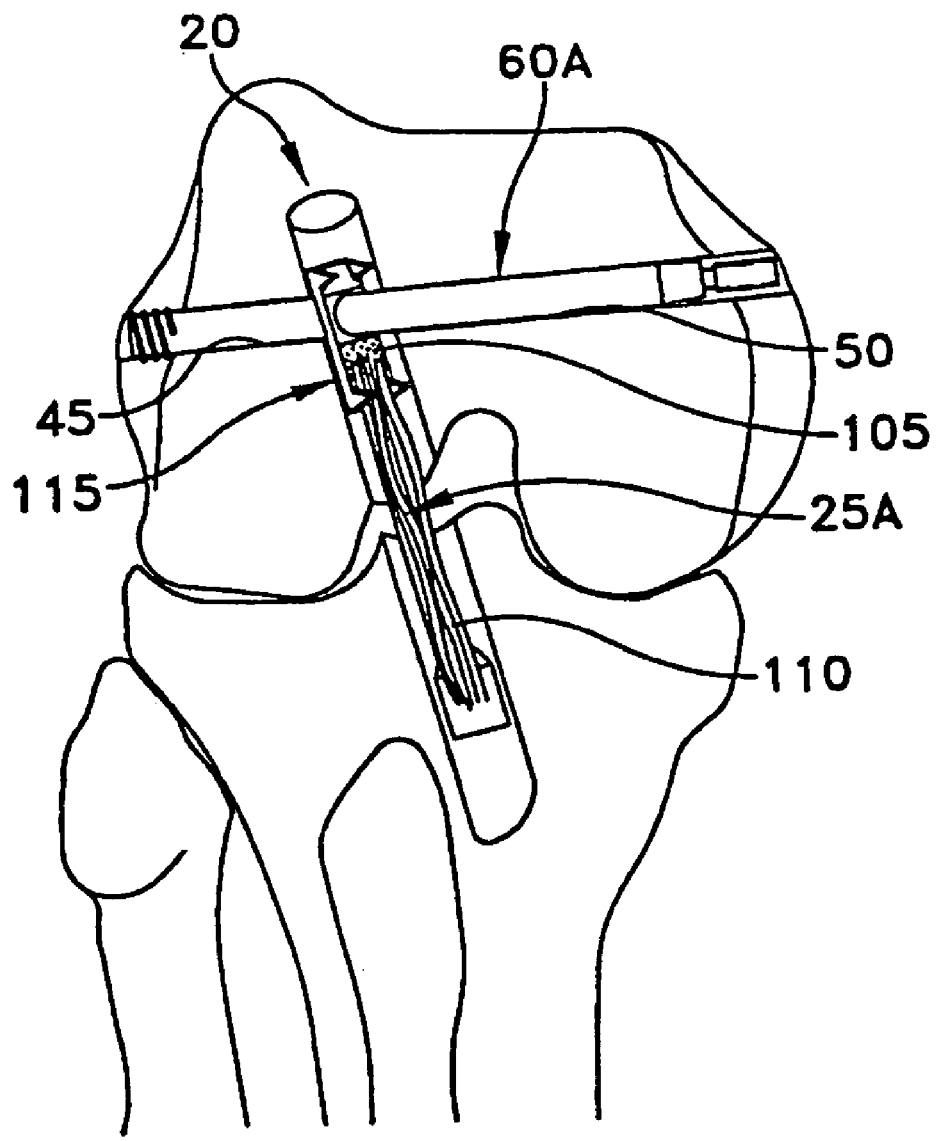
FIG. 22 is a schematic view illustrating another crosspinning procedure utilizing a plate and a graft ligament comprising a bone block.

Looking next at FIG. 22, it is also possible to use crosspin 60A in conjunction with plate 115. In this case it is desirable to size the plate's opening 125 so that it will make a snug fit with the shaft of crosspin 60A, whereby the crosspin will drive the plate laterally against the side wall of femoral tunnel 35, whereby to fix graft ligament 25A in position.

With respect to the plate-and-bone-block-based crosspinning techniques described above and illustrated in FIGS. 19–22, it should also be appreciated that while the techniques have been discussed in the context of the aforementioned crosspins 135 and 60A, they may also be practiced equally well with the crosspins 60 and 60B discussed above, as well as with other crosspins well known in the art.

The inventions discussed in the preceding sections can be comprised of any material applicable to orthopedic fixation devices such as implantable metallic, polymeric, composite, biologic or ceramic materials. However, in the case of the non-cannulated crosspins 60 and 60A, the solid cross-section unique to non-cannulated devices provides shear strength greater than that of similar diameter cannulated devices. Connection features, such as the openings 70 and threads 90, allow the non-cannulated crosspins 60 and 60A to be pulled through the knee and placed without any of the cross-sectional area being used for guidance tools such as the flexible member 55. This additional cross-sectional area helps to strengthen the portion of the crosspin that is under load by the ACL graft in actual clinical use. This consequently allows the non-cannulated crosspin with solid cross-sectional area to be made from a material which is typically weaker in shear strength than metal, such as non-absorbable or absorbable polymeric, composite, biologic or ceramic biomaterials, without significantly compromising the crosspin holding strength.

What is claimed is:

1. A crosspin for supporting a graft ligament in a first bone tunnel formed in a bone, by positioning the crosspin in a second bone tunnel extending transverse to, and intersecting, the first bone tunnel, said crosspin comprising:
    a shaft comprising a distal portion, an intermediate portion, and a proximal portion;
    said distal portion comprising attachment means for attaching a flexible member to said shaft;
    said intermediate portion comprising screw threads; and
    said proximal portion comprising driver engagement structure for engagement by a driver adapted to turn said shaft;
    wherein said crosspin is adapted to be drawn through the second bone tunnel by the flexible member attached to said distal portion attachment means, and
    said crosspin screw threads are adapted to be turned into the bone by the driver engaged with said engagement means; and
    a connector for releasably connecting said distal portion to said intermediate portion, such that said distal portion is separable from said intermediate portion.

2. A crosspin according to claim 1 wherein said intermediate portion comprises a solid shaft, and further wherein said attachment means comprises at least one opening formed in said distal portion.

3. A crosspin for supporting a graft ligament in a first bone tunnel formed in a bone, by positioning the crosspin in a second bone tunnel extending transverse to, and intersecting, the first bone tunnel, said crosspin comprising:
    a shaft comprising a distal portion, an intermediate portion, and a proximal portion;
    said distal portion having a flexible member attached thereto;
    said intermediate portion comprising screw threads; and
    said proximal portion including driver engagement structure for engagement by a driver adapted to turn said shaft;
    wherein said crosspin is adapted to be drawn through the second transverse bone tunnel by the flexible member, and said crosspin screw threads are adapted to be turned into the bone by a driver engaged with said engagement means; and
    said crosspin further comprises a connector for releasably connecting said distal portion to said intermediate portion, such that said distal portion is releasably connected to said intermediate portion.

4. A crosspin according to claim 3 wherein said connector comprises a screw mount.

5. A crosspin for supporting a graft ligament in a first bone tunnel formed in a bone, by positioning the crosspin in a second bone tunnel extending transverse to, and intersecting, the first bone tunnel, said crosspin comprising:
    a cannulated shaft comprising a distal portion, an intermediate portion, and a proximal portion;
    said intermediate portion being provided with external screw threads; and
    said proximal portion comprising driver engagement structure for engagement by a cannulated driver adapted to turn said shaft;
    wherein said crosspin is adapted to be positioned in the second transverse bone tunnel by loading said crosspin on, and moving said crosspin along, a flexible member, and said crosspin is provided with screw threads adapted to be turned into the bone by the driver engaged with said driver engagement means; and
    said shaft further comprises a screw mount releasably connecting said distal portion to said intermediate portion, such that at least said distal portion is adapted to be removed from said intermediate portion.

* * * * *